United States Patent
Schleich et al.

(10) Patent No.: US 10,071,246 B2
(45) Date of Patent: Sep. 11, 2018

(54) SELECTIVE STIMULATION WITH COCHLEAR IMPLANTS

(71) Applicant: MED-EL Elektromedizinische Geraete GmbH, Innsbruck (AT)

(72) Inventors: Peter Schleich, Telfs (AT); Dirk Meister, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 32 days.

(21) Appl. No.: 15/194,649

(22) Filed: Jun. 28, 2016

(65) Prior Publication Data

US 2016/0375244 A1    Dec. 29, 2016

Related U.S. Application Data

(60) Provisional application No. 62/185,766, filed on Jun. 29, 2015.

(51) Int. Cl.
  *A61N 1/00* (2006.01)
  *A61N 1/36* (2006.01)
  *A61N 1/05* (2006.01)

(52) U.S. Cl.
  CPC ..... *A61N 1/36032* (2013.01); *A61N 1/36036* (2017.08); *A61N 1/0541* (2013.01)

(58) Field of Classification Search
  CPC ............. A61N 1/0541; A61N 1/36032; A61N 1/36036
  See application file for complete search history.

(56) References Cited

U.S. PATENT DOCUMENTS

| | | | |
|---|---|---|---|
| 7,899,547 B1 | 3/2011 | Emadi et al. | |
| 7,941,223 B2 | 5/2011 | Zierhofer et al. | |
| 8,412,340 B2 * | 4/2013 | Litvak | A61N 1/36032 607/136 |
| 2009/0132005 A1 | 5/2009 | van den Honert et al. | |
| 2010/0185261 A1 | 7/2010 | Schleich | |
| 2011/0077710 A1 | 3/2011 | Saoji et al. | |

(Continued)

OTHER PUBLICATIONS

International Searching Authority, International Search Report—International Application No. PCT/US16/39717, dated Sep. 15, 2016, together with the Written Opinion of the International Searching Authority, 13 pages.

*Primary Examiner* — George Manuel
(74) *Attorney, Agent, or Firm* — Sunstein Kann Murphy & Timbers LLP

(57) ABSTRACT

A signal processing arrangement generates electrode stimulation signals to stimulation contacts in a cochlear implant electrode array. A signal filter bank transforms an input sound signal into band pass signals, which each represent an associated frequency band of audio frequencies. A signal processing module processes the band pass signals in a sequence of sampling time frames, wherein for each time frame, the processing includes performing a spectral feature analysis of the band pass signals, and dynamically assigning a stimulation focus pattern to one or more of the band pass signals based on the spectral feature analysis. A stimulation coding module is configured to code the processed band pass signals for each time frame to produce the electrode stimulation signals for delivery by the stimulation contacts to a region of adjacent auditory neural tissues.

16 Claims, 7 Drawing Sheets

(56) References Cited

U.S. PATENT DOCUMENTS

| | | |
|---|---|---|
| 2011/0230933 A1 | 9/2011 | Choi et al. |
| 2012/0209351 A1 | 8/2012 | Meister et al. |
| 2013/0046359 A1* | 2/2013 | James ................ A61N 1/36032 607/57 |
| 2014/0074183 A1 | 3/2014 | Kulkarni et al. |

* cited by examiner

SELECTIVE STIMULATION WITH COCHLEAR IMPLANTS

This application claims priority from U.S. Provisional Patent Application 62/185,766, filed Jun. 29, 2016, which is incorporated herein by reference in its entirety.

FIELD OF THE INVENTION

The present invention relates to cochlear implant systems, and more specifically, to techniques for coding electrical stimulation pulses in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, this electrode array 110 includes multiple stimulation contacts 112 on its surface that provide selective stimulation of the cochlea 104. Depending on context, the stimulation contacts 112 are also referred to as electrode channels. In cochlear implants today, a relatively small number of electrode channels are each associated with relatively broad frequency bands, with each stimulation contact 112 addressing a group of neurons through an electric stimulation pulse having a charge which is derived from the instantaneous amplitude of the signal envelope within that frequency band.

In some coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing.

For example, FIG. 2 shows the major functional blocks in a typical cochlear implant signal processing system wherein band pass signals are processed and coding to generate electrode stimulation signals to stimulation electrodes in an implanted cochlear implant electrode array. Preprocessor Filter Bank 201 pre-processes the initial acoustic audio signal with a bank of band pass filters, each of which is associated with a specific band of audio frequencies so that the acoustic audio signal is filtered into some M band pass signals, $B_1$ to $B_M$ where each signal corresponds to the band of frequencies for one of the band pass filters. Based on the tonotopic organization of the cochlea, each stimulation contact in the scala tympani often is associated with a specific band pass filter of the external filter bank. FIG. 3 shows an example of a short time period of an audio speech signal from a microphone, and FIG. 4 shows an acoustic microphone signal decomposed by band-pass filtering by a bank of filters into a set of signals.

The band pass signals $B_1$ to $B_M$ are input to a Signal Processor 202 which extracts signal specific stimulation information—e.g., envelope information, phase information, timing of requested stimulation events, etc.—into a set of N stimulation channel signals $S_1$ to $S_N$ that collectively represent the sound information that is present in the initial acoustic audio signal. Stimulation Coding Module 203 then converts the processed stimulation channel signals $S_1$ to $S_N$ to produce a corresponding sequence of electrode stimulation signals $A_1$ to $A_M$ that provide an optimal electric representation of the acoustic signal, while the Pulse Mapping and Shaping Module 204 then applies a linear mapping function (typically logarithmic) and pulse shaping of the electrode stimulation signals $A_1$ to $A_M$ that is adapted to the needs of the individual implant user based on a post-surgical fitting process that determines patient-specific perceptual characteristics.

The output of the Pulse Mapping and Shaping Module 204 is a set of electrode stimulation signals $E_1$ to $E_M$ to the stimulation contacts in the implanted electrode array which stimulate the adjacent nerve tissue. Symmetrical biphasic current pulses are often applied for stimulation. In the specific case of a CIS system, the stimulation pulses are applied in a strictly non-overlapping sequence. Thus, as a typical CIS-feature, only one electrode channel is active at one time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor ($Q\approx3$) of the filters. In case of a voiced speech segment, this envelope is approximately periodic, and the repetition rate is equal to the pitch frequency.

In the existing CIS-strategy, only the signal envelopes are used for further processing, i.e., they contain the entire stimulation information. For each electrode channel, the signal envelope is represented as a sequence of biphasic pulses at a constant repetition rate. A characteristic feature of CIS is that this repetition rate (typically 1.5 kpps) is equal for all electrode channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Another cochlear implant stimulation strategy that transmits fine time structure information is the Fine Structure Processing (FSP) strategy by Med-El. Zero crossings of the band pass filtered time signals are tracked, and at each negative to positive zero crossing a Channel Specific Sampling Sequence (CSSS) is started. Typically CSSS sequences are only applied on the first one or two most apical electrode channels, covering the frequency range up to 200 or 330 Hz. The FSP arrangement is described further in Hochmair I, Nopp P, Jolly C, Schmidt M, SchoBer H, Garnham C, Anderson I, *MED-EL Cochlear Implants: State of the Art and a Glimpse into the Future*, Trends in Amplification, vol. 10, 201-219, 2006, which is incorporated herein by reference.

Many CI coding strategies use what is referred to as an N-of-M approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

One method to reduce the spectral clustering of stimulation per time frame is the MP3000™ coding strategy by Cochlear Ltd, which uses a spectral masking model on the electrode channels. Another method that inherently enhances coding of speech onsets is the ClearVoice™ coding strategy used by Advanced Bionics Corp, which selects electrode channels having a high signal to noise ratio. U.S. Patent Publication 2005/0203589 describes how to organize electrode channels into two or more groups per time frame. The decision which electrode channels to select is based on the amplitude of the signal envelopes.

In addition to the specific processing and coding approaches discussed above, different specific pulse stimulation modes are possible to deliver the stimulation pulses with specific stimulation contacts—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc. But some stimulation arrangements are quite power consuming, especially when neighboring stimulation contacts are used as current sinks. Up to 10 dB more charge might be required than with simple mono-polar stimulation concepts (if the power-consuming pulse shapes or stimulation modes are used continuously).

Another consideration as to stimulation pattern is the spread of the excitation pattern in the stimulated neural tissue. This excitation spread is a function of amplitude so that at relatively low stimulation levels near the hearing threshold level, the region of excited neurons is small, whereas at high stimulation levels, large populations throughout the cochlea are excited. See, e.g., U.S. Pat. No. 7,941,223, which is incorporated herein by reference in its entirety. Excitation spread occurs both with acoustic excitation (as in normal hearing) and with electric stimulation of the neural tissue as in a cochlear implant.

Some literature in the field discusses stimulation modes intended to produce selective stimulation; e.g. U.S. Pat. No. 7,899,547; EP 2482923, and Litvak et al., *Loudness growth observed under partially tripolar stimulation: Model and data from cochlear implant listeners*, J. Acoust. Soc. Am. 122 2, August 2007; all of which are incorporated herein by reference in their entireties. Such literature takes into account the natural behavior of a level-dependent spread of excitation. At high perceptual levels, stimulation modes intending to generate focused stimulation, produce a spread of excitation that is quite similar to the spread of a simple mono-polar stimulation mode. For a wide spread of excitation, mono-polar stimulation is probably the most power-efficient mode, whereas at low stimulation levels, multi-polar stimulation is known to achieve the lowest spread of excitation, albeit in a less power efficient manner.

SUMMARY OF THE INVENTION

Embodiments of the present invention are directed to a signal processing arrangement and corresponding method that generates electrode stimulation signals to stimulation contacts in a cochlear implant electrode array. A signal filter bank is configured to transform an input sound signal into band pass signals that each represent an associated frequency band of audio frequencies. A signal processing module is configured to process the band pass signals in a sequence of sampling time frames, wherein for each time frame, the processing includes performing a spectral feature analysis of the band pass signals, and dynamically assigning a stimulation focus pattern to one or more of the band pass signals based on the spectral feature analysis. A stimulation coding module is configured to code the processed band pass signals for each time frame to produce the electrode stimulation signals for delivery by the stimulation contacts to a region of adjacent auditory neural tissue.

In further specific embodiments, there may be a pulse mapping and shaping module that is configured to weight the electrode stimulation signals based on patient-specific stimulation characteristics.

The signal processing module may specifically be configured to dynamically assign a focused stimulation pattern to one or more of the band pass signals based on the spectral feature analysis so that the electrode stimulation signals are delivered to a region of adjacent auditory neural tissue that is limited by the stimulation focus pattern. For example, the focused stimulation pattern may be based on a tripolar stimulation mode or a phased array stimulation mode.

In addition or alternatively, the signal processing module may specifically be configured to dynamically assign an unfocused stimulation pattern to one or more of the band pass signals based on the spectral feature analysis so that the electrode stimulation signals are delivered to a region of adjacent auditory neural tissue that is not limited by the stimulation focus pattern. For example, the unfocused stimulation pattern may be based on a monopolar stimulation mode. The signal processing module may be configured to perform a spectral feature analysis of the band pass signals that includes an analysis of frequency spread of spectral features of a plurality of adjacent band pass signals.

DETAILED DESCRIPTION OF SPECIFIC EMBODIMENTS

The width of spectral features has been accounted for in coding strategies which are based on the N-of-M principle where N channels which higher amplitudes are selected for stimulation. Channels which contain dominant spectral features are more likely to be selected. In presence of a broad and dominant spectral feature which is spread over adjacent channels, a less dominant and narrow spectral feature is likely to be omitted. Besides these implications related to channel selection based on amplitudes only, no further measure is taken to code the spectral widths of the features by means of manipulating stimulation pulses or stimulation modes, e.g. monopolar, tripolar.

Embodiments of the present invention take account of level-dependent spread of excitation based on assigning focused or unfocused stimulation patterns to stimulation channels as a function of a channel independent analysis of the spectral widths of spectral features of the digital input signal. The selected focused/unfocused stimulation patterns may be applied by the signal coding stage which applies a selected coding strategy to present the assigned stimulation patterns to the stimulation electrodes of the CI electrode contacts. A focused stimulation pattern may be realized (for example) by tripolar or phased array stimulation modes to deliver electrode stimulation signals to a limited region of adjacent neural auditory tissue. Alternatively, an unfocused stimulation focus pattern may be realized by (for example) by conventional monopolar stimulation modes to deliver electrode stimulation signals to a region of adjacent neural auditory tissue that is not limited by the stimulation focus pattern. In some specific embodiments, the dynamic focusing assignment may result in a mixture of focused and unfocused stimulation patterns.

When the focusing assignment is done dynamically, overall power consumption by the system may be comparable to the power consumption of existing cochlear implant systems. In some embodiments, the assignment stimulation patterns may occur dynamically such that energy consuming focused stimulation patterns are assigned rather rarely. And in contrast to previous arrangements for handling spread of excitation, embodiments of the present invention are specific to the signal processing stage, and so the invention is not limited to any particular specific coding strategy (such as CIS, FSP, FSP 4, N-of-M, etc.). And since some features of the audio signal that are analyzed by the signal processing stage may be band-specific, while other signal features may be characteristic of portions of the input signal that may be larger or smaller than a single band pass channel. Therefore (and contrary to the suggestion of the prior art), where the focus assignment step analyzes the frequency spread (FS) of spectral features over a plurality of bands of the band pass signals.

Figure 1:
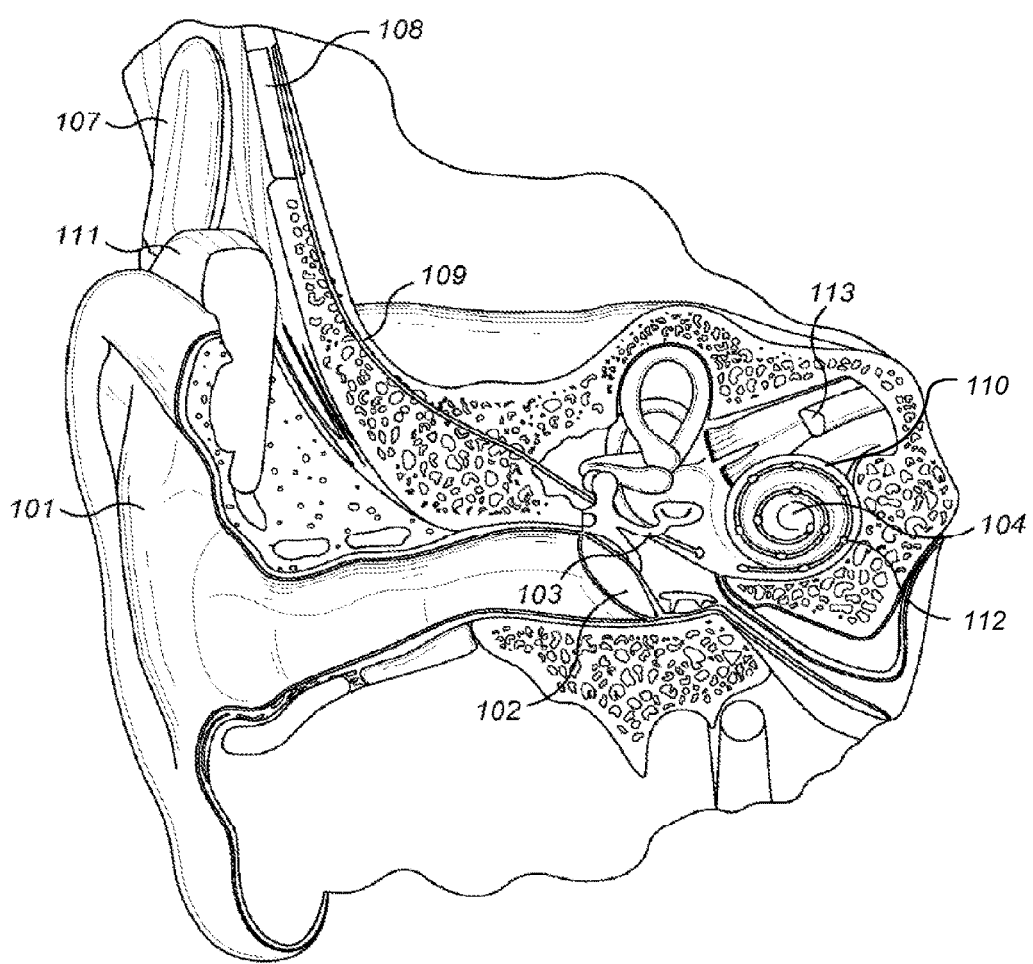
FIG. 1 shows a section view of a human ear with a typical auditory prosthesis system designed to deliver electric stimuli to the inner ear and acoustic stimuli at the ear canal.
Figure 2:
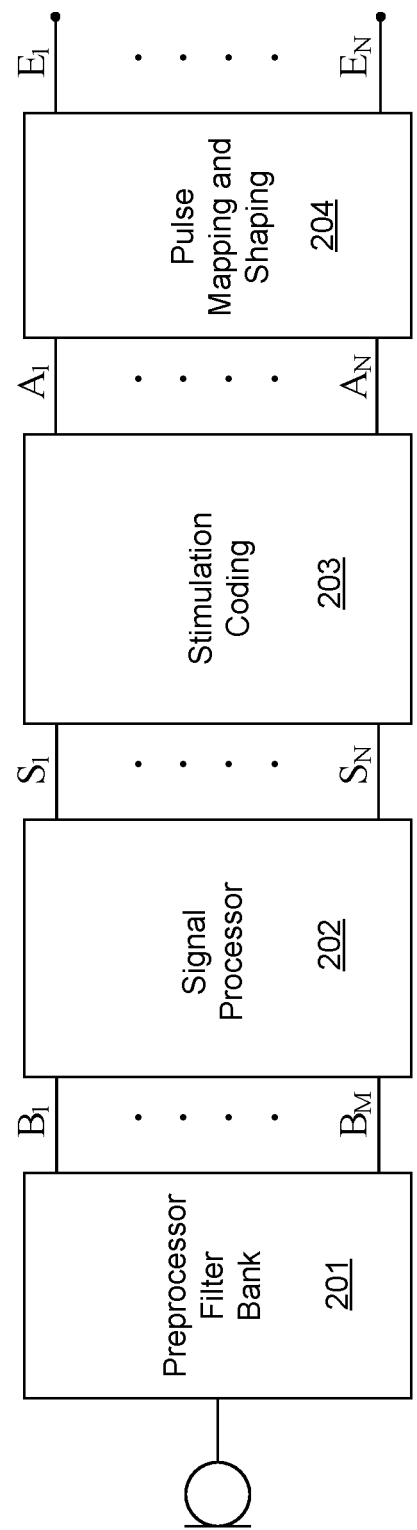
FIG. 2 shows various functional blocks in a continuous interleaved sampling (CIS) processing system.
Figure 3:
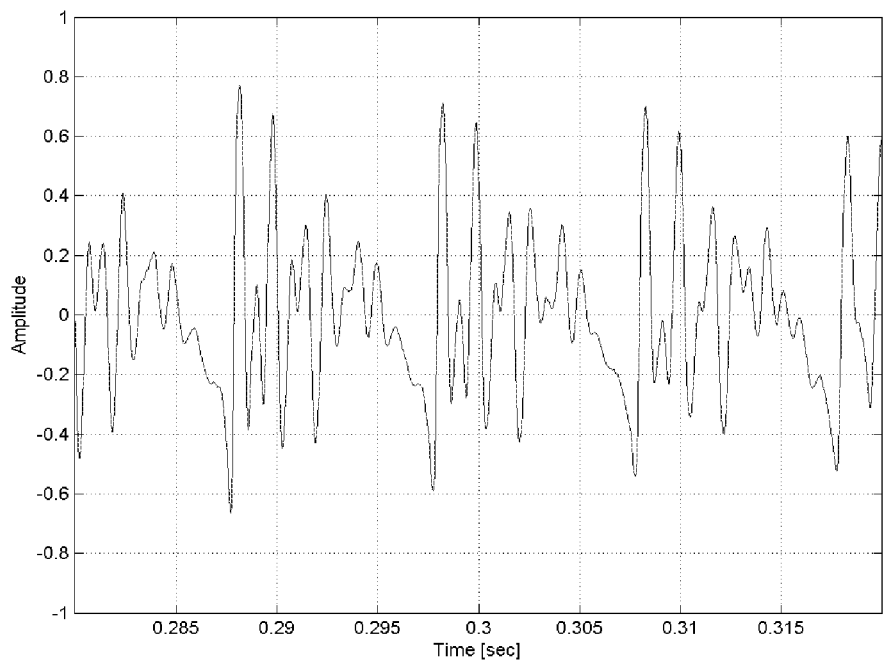
FIG. 3 shows an example of a short time period of an audio speech signal from a microphone.
Figure 4:
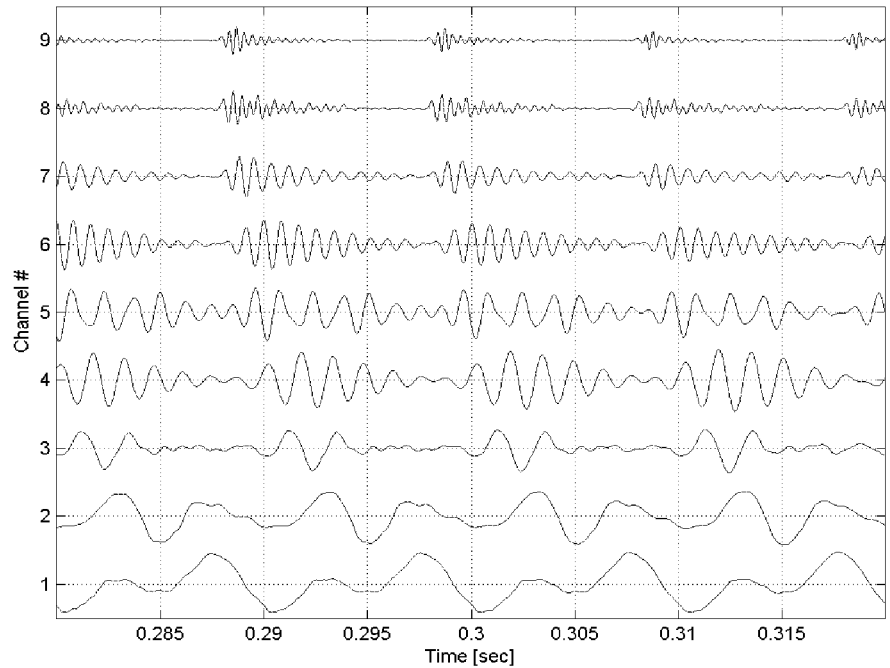
FIG. 4 shows an acoustic microphone signal decomposed by band-pass filtering by a bank of filters into a set of signals.

Embodiments of the present invention are directed to a signal processing arrangement and corresponding method that generates electrode stimulation signals to stimulation contacts in a cochlear implant electrode array based on determining the frequency spread or spectral features of the band pass signals. As in the arrangement discussed above with respect to FIG. 2, a preprocessor signal filter bank 201 can be configured to transform an input sound signal into band pass signals $B_1$ to $B_M$ that each represent an associated frequency band of audio frequencies.

Then the signal processing module 202 can be configured to process the band pass signals $B_1$ to $B_M$ in a sequence of sampling time frames that includes performing a spectral feature analysis of the band pass signals such as an analysis of frequency spread of spectral features of the adjacent band pass signals. Based on that spectral feature analysis, the signal processing module 202 then dynamically assigns a stimulation focus pattern to one or more of the band pass signals. The signal processing module 202 may specifically be configured to dynamically assign a focused stimulation pattern such as a tripolar stimulation mode or a phased array stimulation mode to one or more of the band pass signals $B_1$ to $B_M$ based on the spectral feature analysis so that the electrode stimulation signals are delivered to a region of adjacent auditory neural tissue that is limited by the stimulation focus pattern. In addition or alternatively, the signal processing module 202 may specifically be configured to dynamically assign an unfocused stimulation pattern such as a monopolar stimulation mode to one or more of the band pass signals $B_1$ to $B_M$ based on the spectral feature analysis so that the electrode stimulation signals are delivered to a region of adjacent auditory neural tissue that is not limited by the stimulation focus pattern.

The stimulation coding module 203 then is configured to convert the processed stimulation channel signals $S_1$ to $S_N$ to produce a corresponding sequence of electrode stimulation signals $A_1$ to $A_M$ that provide an optimal electric representation of the acoustic signal, while the Pulse Mapping and Shaping Module 204 then applies a linear mapping function (typically logarithmic) and pulse shaping of the electrode stimulation signals $A_1$ to $A_M$ that is adapted to the needs of the individual implant user based on a post-surgical fitting process that determines patient-specific perceptual characteristics.

In the following discussion, the focused stimulation pattern specifically discussed is the tripolar stimulation mode, which comprises a stimulation pulse of a given polarity applied by a given stimulation contact, accompanied by offsetting stimulation pulses of opposite polarity on the adjacent neighboring stimulation contacts (all three pulses being charge balanced to avoid net DC current). Since these current sources and sinks are physically close together, and since the endolymph fluid in the cochlea has high electrical conductivity, the region of neural tissue that is stimulated is fairly focused and limited. Conventional monopolar stimulation, by contrast, is used as the unfocused stimulation focus pattern and exploits the electrical stimulation that results from a single intracochlear stimulation contact together with a remote extracochlear ground electrode contact that completes the current path, and the resulting region of neural tissue that is stimulated is fairly unfocused and not limited.

More specifically with respect to the dynamic focusing assignment performed by the signal processing module 202, it may initially may process the incoming band pass signals $B_1$ to $B_M$ such that for each frequency band pass signal Bn, a characteristic amplitude level $A_n$ is determined, which may specifically be the amplitude value of the center frequency of the frequency band or a mean amplitude value of the band. And for each band Bn, the differences are calculated between the characteristic amplitude levels of adjacent bands are calculated, including the sign of the difference which determines whether the slope of the amplitude curve is rising or falling: $D1=(A_{n-1}-A_n)$ and $D2=(A_n-A_{n+1})$. Then for each band Bn, the two differences to the left and right neighbors, D1 and D2, are compared and a focused/unfocused assignment is made.

Figure 5:
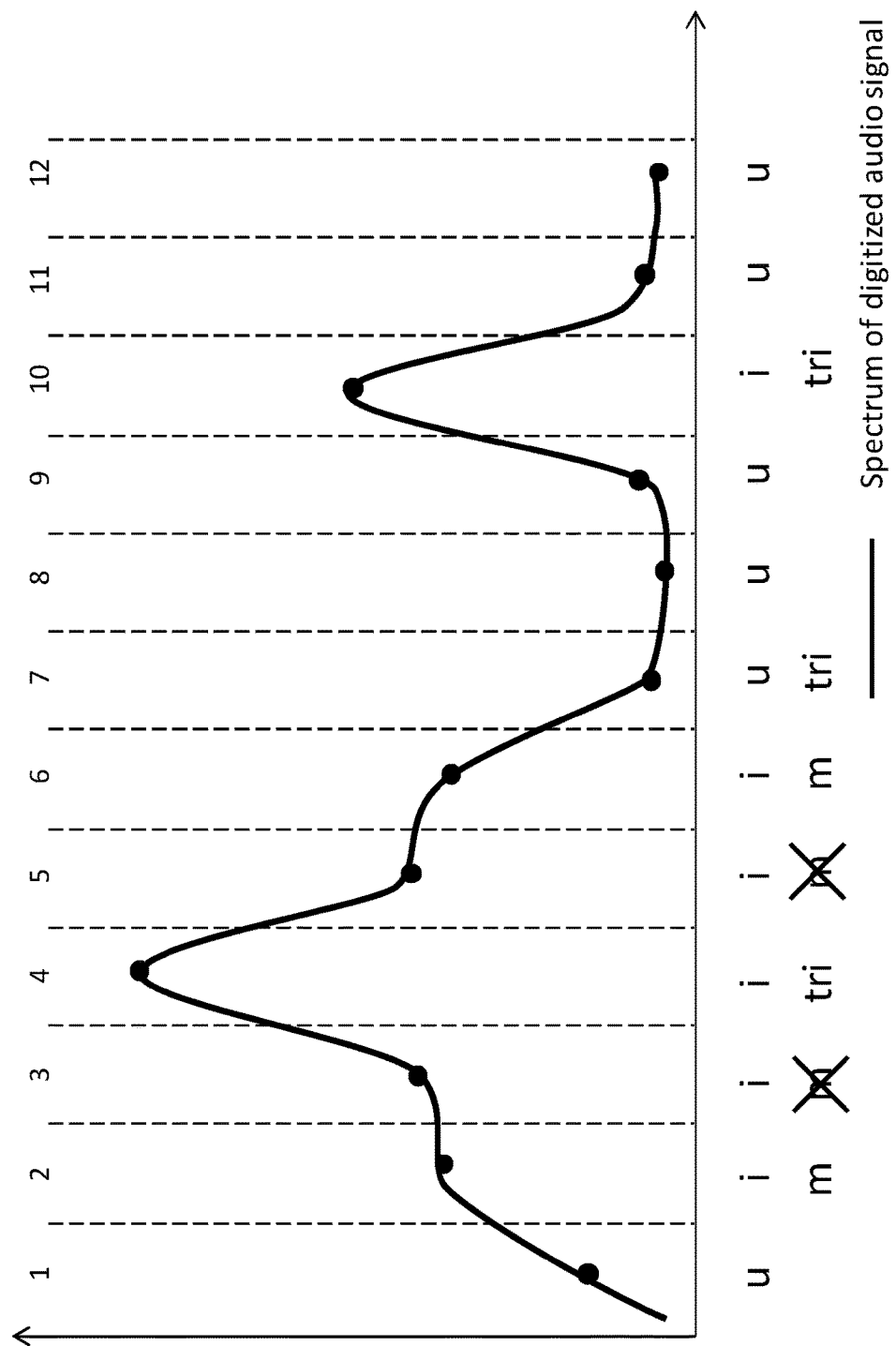
FIG. 5 shows an example of a band pass signal spectrum assignment graph according to a first scenario.

FIG. 5 shows band pass amplitude signals for a first scenario where, if the absolute value of only one of the amplitude differences D1 and D2 is greater than some given first focus threshold value X, that band pass channel may be evaluated as important ("i" in FIG. 5), and have assigned to it an unfocused stimulation pattern; see channels 2, 3, 5, and 6. The first focus threshold value X can be predetermined or dynamically determined, e.g. by averaging the actual differences D between all adjacent channels, or as a fraction of the amplitude of the maximum channel.

If the absolute values of both adjacent channel differences D1 and D2 are larger than the focus threshold value X, and the sign of the differences is different (one is positive and the other negative), then that channel may evaluated important ("i") and a focused stimulation pattern may be assigned; see e.g., channels 4 and 10.

Figure 8:
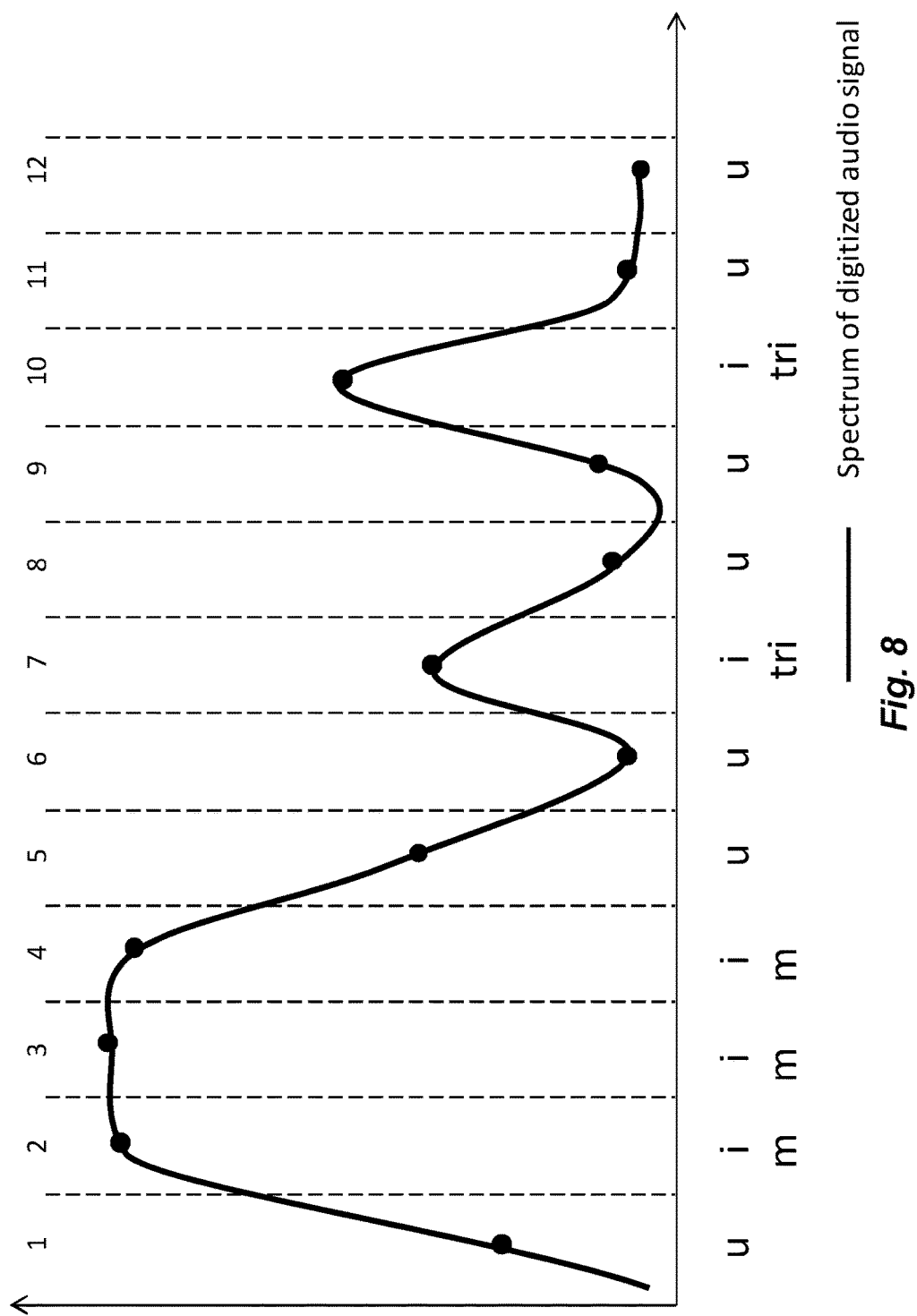
FIG. 8 shows an example of a band pass signal spectrum assignment graph according to a fourth scenario.

If the absolute values of both differences D1 and D2 are smaller than a second focus threshold value Y, and the absolute value of the characteristic amplitude level of this band ($A_n$) is greater than another third focus threshold value, W, then that channel is evaluated important ("i") and an unfocused stimulation pattern may be assigned; see, e.g., FIG. 8, channel 3. Again, either both of the second focus threshold value, Y, and the third focus threshold value, W, can be fixed, or dynamically determined; e.g., adjusted relative to the amplitude of the maximum channel. Any or all of the thresholds X, Y, and W also might be a relative threshold on a logarithmic scale, e.g. ½/2 or 6 dB.

All the other band pass channels may be evaluated as unimportant ("u") and no focused/unfocused stimulation pattern may be assigned (see e.g., FIG. 5, channels 8 and 12) or the stimulation focus pattern may be determined based on the neighboring channels (e.g., FIG. 5, channels 9 and 11).

There needs to be different rules for determining the stimulation focus patterns for the stimulation contacts at the apical and basal ends of the electrode array. One way to handle these is to provide additional analysis-only filter bands on the "empty" sides of these stimulation contacts, and then follow the same analysis rules set forth above. Thus, in the specific examples set forth in FIGS. 5-9, Channels 1 and 12 are such empty analysis-only frequency bands, and the implanted electrode array has ten stimulation contacts that correspond to Channels 2-11 in those Figures.

As can be seen in FIG. 5, conflicting results can arise when determining a stimulation mode to realize focused or unfocused stimulation. For example, if the applied stimulation modes are monopolar for unfocused stimulation and tripolar for focused stimulation, Channels 3 and 5 in FIG. 5 are assigned for monopolar stimulation based on the evaluation described above of their own channels, while at the same time they have been assigned for the opposite polarity stimulation portion of the tripolar stimulation mode based on the evaluation of their common neighboring Channel 4. In a case where simultaneous stimulation of the stimulation channels is desired, another rule may be applied which follows the principle that the highest characteristic amplitude level of the involved channels (Channel 4 in this case) overrules the other focusing mode assignments of Channels 3 and 5. This would lead to tripolar stimulation on Channels 3, 4 and 5 with one polarity on Channel 4 and opposite polarities on Channels 3 and 5, instead of monopolar stimulation on Channels 3 and 5. In a sequential stimulation mode arrangement, first the focused stimulation is applied with Channel 4 in the center (focus) and Channels 3 and 5 as the adjacent current sinks. Then, in the next time frame, monopolar stimulation of Channel 3, and then in the next time frame, monopolar stimulation of Channel 5 can be applied, where the sequential order can be changed.

Figure 6:
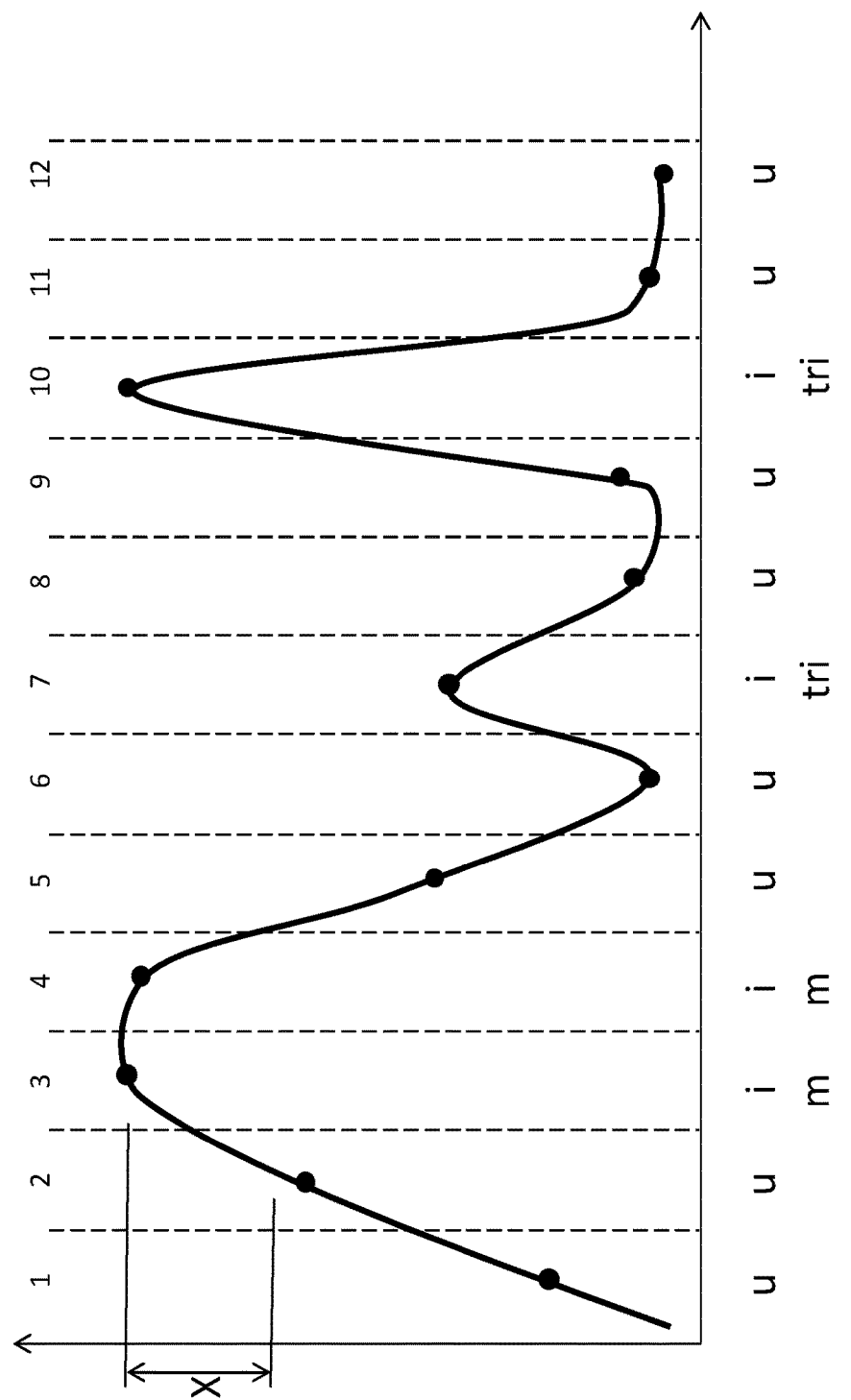
FIG. 6 shows an example of a band pass signal spectrum assignment graph according to a second scenario.
Figure 7:
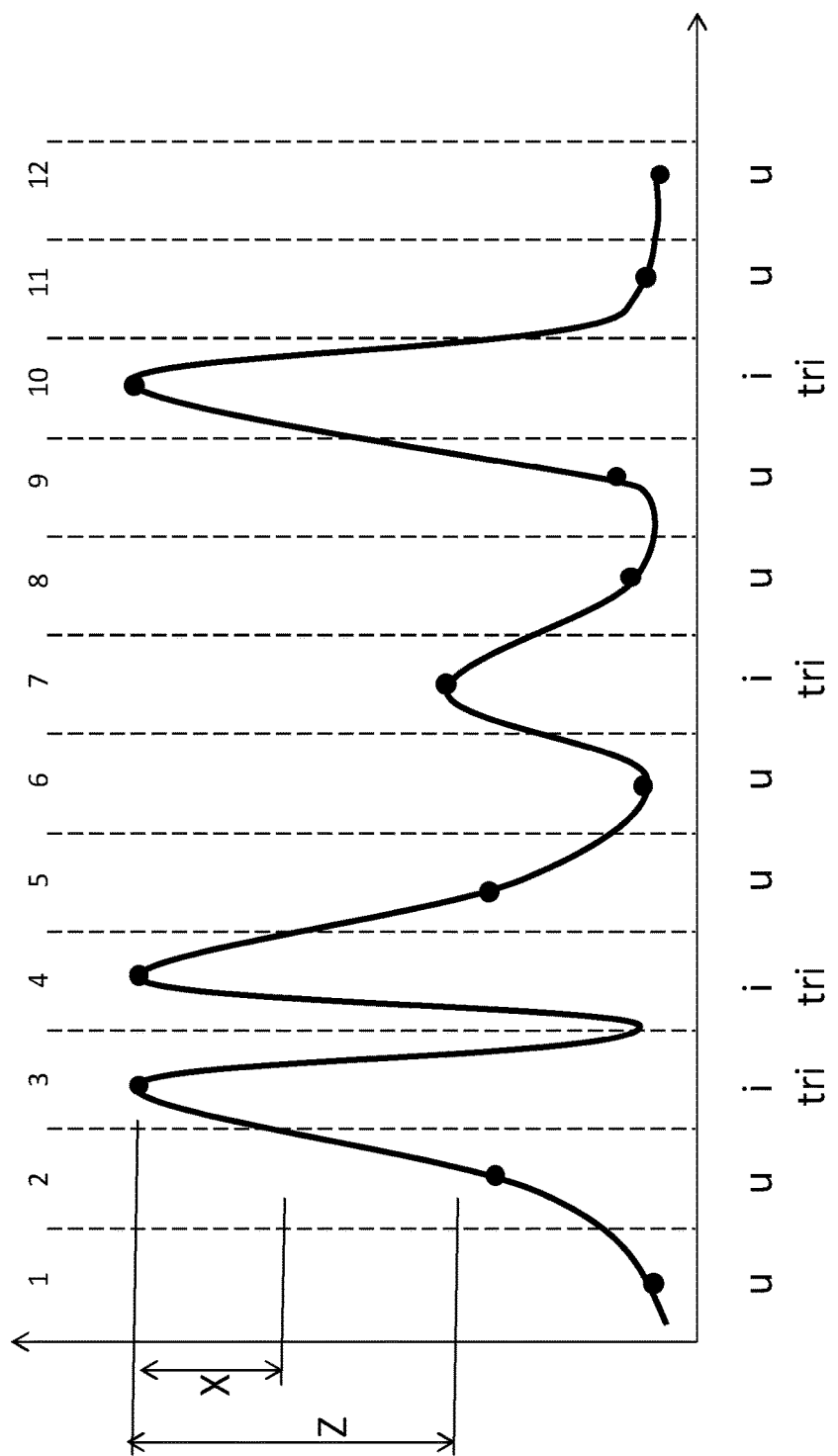
FIG. 7 shows an example of a band pass signal spectrum assignment graph according to a third scenario.

As can be seen from comparison of the assignment scenarios depicted in FIGS. 6 and 7, the assignment of focused or unfocused stimulation (denoted as "m" for monopolar and "tri" for tripolar) may not reflect the actual spectrum of the digital audio signal (solid lines). FIG. 6 shows a single broad peak at Channels 3 and 4 to which monopolar stimulation pattern would be assigned, whereas FIG. 7 shows two adjacent sharp peaks on Channels 3 and 4 to which tripolar stimulation patterns should be assigned according to the above description. With the number of band pass signals shown in the Figures, the above focusing assignment rules would assign unfocused (monopolar) stimulation patterns to both channels. The number of band pass signals may be increased in order to increase the processing resolution. In that case, an additional focusing assignment rule would be used to assign the m band pass signals processed in the signal processing module onto the k (m>k) stimulation channels in the implanted electrode array. If the frequency analysis is fine enough to resolve the frequency spectrum shown in FIG. 7, then sequential focused stimulation can be performed with Channels 3 and 4; for example, in one time frame a tripolar stimulation mode would be applied with Channel 3 in the center and Channels 2 and 4 as current sinks, and in the next time frame, focused stimulation with Channel 4 in the focus and Channels 3 and 5 as current sinks is applied.

Alternatively, the first rule of the above discussion may be amended by an additional rule, that if the first focus threshold X is even greater than another specific focus threshold value Z, then a focused stimulation pattern may be assigned. The Z-threshold can be fixed or dynamically adjusted relative to the amplitude of the maximum channel. This amended assignment rule would result in unfocused stimulation patterns for Channels 3 and 4 in the scenario shown in FIG. 6, and focused stimulation patterns for these channels in scenario 3. If tripolar stimulation mode is chosen for the focused stimulation pattern, then a pattern with same polarities on Channels 3 and 4 have to be used and opposite polarities on Channels lower than 3 and higher than 4.

In the foregoing discussion, the assignment of focused or unfocused stimulation pattern has been described as a sort of digital process, i.e. either focused or unfocused. Some embodiments may be based on a smooth transition between these two stimulation patterns, or a number of intermediate states may be possible as well. Similarly, depending on the actual values of the amplitude differences D1 and D2, a mixture of focused and unfocused stimulation also may be assigned. For example, partial tripolar and partial monopolar stimulation may be assigned at the same time to the same stimulation channel. So if D1 and D2 are large, a pure tripolar stimulation pattern may be assigned (e.g. FIGS. 6 and 7, Channel 10). Or if D1 and D2 are lower (e.g. FIGS. 6 and 7, Channel 7), then a mixture of stimulation patterns may be assigned.

In embodiments of the present invention, the upfront determination of the location and width of band pass filters of the implant system is no longer critical. In existing cochlear implant systems, the band pass filters are chosen such that the expected formants of human voices are well within the frequency bands. And if the design choice is successful, then each pass band signal can be individually analyzed. But speech formant frequencies vary strongly from one person to another, and non-speech sound signals such as music may be important in some situations. This limitation can be avoided in embodiments of the present invention by analyzing multiple frequency bands at once as discussed above, to reliably identify the important frequency features of a sensed sound signal.

Embodiments of the present invention can also realize a significant reduction of power consumption as compared to the combination of conventional existing coding strategies, using more accurate but power consuming stimulation modes. Power-consuming stimulation modes will only be applied to limited portions of the input sound signal. An enhancement of spectro-temporal features at low levels as well as a more natural change of spread of excitation over levels can be modelled with the system.

Embodiments of the invention may be implemented in part any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of signal processing for generating electrode stimulation signals to stimulation contacts in an implanted cochlear implant electrode array, the method comprising:
   transforming an input sound signal into a plurality of band pass signals each representing an associated frequency band of audio frequencies;
   processing the band pass signals in a sequence of sampling time frames, wherein for each time frame, the processing includes:
   i. performing a spectral feature analysis of the band pass signals, including determining a difference in amplitude between each band pass signal and that of adjacent band pass signals;
   ii. dynamically assigning a stimulation focus pattern to one or more of the band pass signals based on whether the difference in amplitude between each band pass signal and its adjacent band pass signals is greater than a focus threshold value; and
   coding the processed band pass signals for each time frame to produce the electrode stimulation signals for delivery by the stimulation contacts to a region of adjacent auditory neural tissue.

2. The method according to claim 1, further comprising: weighting the electrode stimulation signals based on patient-specific stimulation characteristics.

3. The method according to claim 1, wherein dynamically assigning the stimulation focus pattern includes dynamically assigning a focused stimulation pattern to one or more of the band pass signals based on the spectral feature analysis so that the electrode stimulation signals are delivered to a region of adjacent auditory neural tissue that is limited by the stimulation focus pattern.

4. The method according to claim 3, wherein the focused stimulation pattern is based on a tripolar stimulation mode.

5. The method according to claim 3, wherein the focused stimulation pattern is based on a phased array stimulation mode.

6. The method according to claim 1, wherein dynamically assigning the stimulation focus pattern includes dynamically assigning an unfocused stimulation pattern to one or more of the band pass signals based on the spectral feature analysis so that the electrode stimulation signals are delivered to a region of adjacent auditory neural tissue that is not limited by the stimulation focus pattern.

7. The method according to claim 6, wherein the unfocused stimulation pattern is based on a monopolar stimulation mode.

8. The method according to claim 1, wherein the spectral feature analysis of the band pass signals includes an analysis of frequency spread of spectral features of a plurality of adjacent band pass signals.

9. A signal processing arrangement for generating electrode stimulation signals to stimulation contacts in an implanted cochlear implant electrode array, the arrangement comprising:
  a signal filter bank configured to transform an input sound signal into a plurality of band pass signals each representing an associated frequency band of audio frequencies;
  a signal processing module configured to process the band pass signals in a sequence of sampling time frames, wherein for each time frame, the processing includes:
    i. performing a spectral feature analysis of the band pass signals, including determining a difference in amplitude between each band pass signal and that of adjacent band pass signals, and
    ii. dynamically assigning a stimulation focus pattern to one or more of the band pass signals based on whether the difference in amplitude between each band pass signal and its adjacent band pass signals is greater than a focus threshold value; and
  a stimulation coding module configured to code the processed band pass signals for each time frame to produce the electrode stimulation signals for delivery by the stimulation contacts to a region of adjacent auditory neural tissue.

10. The arrangement according to claim 9, further comprising:
  a pulse mapping and shaping module configured to weight the electrode stimulation signals based on patient-specific stimulation characteristics.

11. The arrangement according to claim 9, wherein the signal processing module configured to dynamically assign a focused stimulation pattern to one or more of the band pass signals based on the spectral feature analysis so that the electrode stimulation signals are delivered to a region of adjacent auditory neural tissue that is limited by the stimulation focus pattern.

12. The arrangement according to claim 11, wherein the focused stimulation pattern is based on a tripolar stimulation mode.

13. The arrangement according to claim 11, wherein the focused stimulation pattern is based on a phased array stimulation mode.

14. The arrangement according to claim 9, wherein the signal processing module configured to dynamically assign an unfocused stimulation pattern to one or more of the band pass signals based on the spectral feature analysis so that the electrode stimulation signals are delivered to a region of adjacent auditory neural tissue that is not limited by the stimulation focus pattern.

15. The arrangement according to claim 14, wherein the unfocused stimulation pattern is based on a monopolar stimulation mode.

16. The arrangement according to claim 9, wherein the signal processing module configured to perform a spectral feature analysis of the band pass signals that includes an analysis of frequency spread of spectral features of a plurality of adjacent band pass signals.

* * * * *